US012636233B1

(12) United States Patent
Alshehri et al.

(10) Patent No.: US 12,636,233 B1
(45) Date of Patent: May 26, 2026

(54) PHOSPHORESCENT ENDODONTIC POST

(71) Applicant: KING SAUD UNIVERSITY, Riyadh (SA)

(72) Inventors: Mohammed Abdullah Alshehri, Riyadh (SA); Omar Mohammed Alshehri, Riyadh (SA); Ibraheem Rshood Alqwizany, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 48 days.

(21) Appl. No.: 19/241,290

(22) Filed: Jun. 17, 2025

(51) Int. Cl.
A61C 5/50 (2017.01)
A61K 6/58 (2020.01)
A61K 6/74 (2020.01)

(52) U.S. Cl.
CPC . *A61K 6/58* (2020.01); *A61K 6/74* (2020.01)

(58) Field of Classification Search
CPC .... A61C 5/40; A61C 5/50; A61C 5/55; A61K 6/58; A61K 6/74
USPC .......................................................... 433/224
See application file for complete search history.

(56) References Cited

U.S. PATENT DOCUMENTS 5,102,461 A    4/1992  Rheinberger et al.
5,698,020 A  * 12/1997  Salz ......................... A61K 6/77
                                                          106/35

| | | | | |
|---|---|---|---|---|
| 6,499,995 | B1 * | 12/2002 | Schwartz ................. | A61C 7/00 264/21 |
| 7,125,254 | B2 * | 10/2006 | Calvert .................... | A61C 5/50 433/81 |
| 2003/0124482 | A1 * | 7/2003 | Calvert .................... | A61C 5/50 433/81 |
| 2004/0110111 | A1 * | 6/2004 | Wasylucha ........... | A61C 19/063 433/29 |
| 2005/0026103 | A1 * | 2/2005 | Wasylucha ............. | A61C 3/005 433/29 |
| 2005/0034354 | A1 | 2/2005 | Lunt et al. | |
| 2006/0085005 | A1 | 4/2006 | Kenealy, III et al. | |
| 2006/0194172 | A1 * | 8/2006 | Loveridge ................ | A61K 6/30 106/35 |
| 2009/0047634 | A1 * | 2/2009 | Calvert .................... | A61C 5/50 433/81 |
| 2017/0002264 | A1 | 1/2017 | Kawataki et al. | |
| 2017/0079757 | A1 * | 3/2017 | Karazivan .............. | A61C 7/146 |
| 2020/0055779 | A1 | 2/2020 | Theelke et al. | |
| 2021/0046211 | A1 | 2/2021 | Desinger et al. | |
| 2024/0148481 | A1 * | 5/2024 | Arnold .................... | B28B 3/025 |
| 2025/0032367 | A1 | 1/2025 | Yang et al. | |

* cited by examiner

*Primary Examiner* — Matthew M Nelson
(74) *Attorney, Agent, or Firm* — Nath, Goldberg & Meyer; Joshua B. Goldberg

(57) ABSTRACT

A phosphorescent endodontic post includes a fiber-reinforced composite material including a polymeric matrix and reinforcing fibers; and phosphorescent particles dispersed within the polymer matrix. The phosphorescent particles are configured to emit visible light for about 5 minutes to about 10 minutes following activation by a standard dental curing lamp operating in the 400 nm-500 nm spectrum. In an embodiment, the phosphorescent particles can include europium-doped strontium aluminate. In an embodiment, phosphorescent particles are uniformly dispersed throughout the polymer matrix.

20 Claims, 3 Drawing Sheets

PHOSPHORESCENT ENDODONTIC POST

FIELD AND BACKGROUND OF THE INVENTION

The disclosure of the present patent application relates to endodontic posts and, in particular, phosphorescent endodontic posts.

DESCRIPTION OF THE PRIOR ART

A human tooth comprises a crown, visible above the gumline, and roots anchored to the maxillary or mandibular bones. Within these roots are root canals containing pulp tissue comprising nerves and blood vessels. When this pulp becomes infected or inflamed due to dental caries or physical trauma, endodontic therapy (commonly known as root canal treatment) becomes necessary.

The standard protocol for endodontic therapy involves removing diseased pulp, cleaning and shaping the root canal, and filling it with biocompatible materials. In teeth with significant coronal structure loss, endodontic posts are placed within the canal to provide structural support for the final restoration (crown).

Fiber-reinforced composite posts were first developed and patented in France (ComposiPost/C-Post). These early carbon fiber posts offered significant mechanical advantages—high strength, fatigue resistance, and a low elastic modulus (18-20 GPa) similar to natural dentin. This biomechanical compatibility allows fiber posts to absorb and dissipate masticatory and traumatic stress in a manner similar to natural dentin, protecting the root from fracture and allowing for retreatment if necessary.

Current literature indicates that 15-20% of root canal treatments require retreatment due to reinfection or treatment failure. Approximately 25% of these retreatment cases involve a post that must be removed before the canal can be reaccessed. This removal process presents significant technical challenges due to the optical properties of conventional fiber posts.

The primary difficulty in removing fiber posts arises from their optical transparency within the root canal, creating poor visual distinction between the post and surrounding dentin. This lack of contrast significantly increases the risk of iatrogenic errors during post removal, including but not limited to canal perforation, dentin gouging, ledge formation, unnecessary dentin removal, and creation of false canals-all of which compromise the long-term prognosis of the tooth.

Despite advancements, none of the existing technologies specifically addresses the challenge of safely removing fiber posts during endodontic retreatment.

Accordingly, an endodontic post solving the aforementioned problems is desired.

SUMMARY OF THE INVENTION

A phosphorescent endodontic post maintains the biomechanical advantages of fiber-reinforced posts while substantially improving visibility during retreatment procedures.

According to an embodiment, a phosphorescent endodontic post includes a fiber-reinforced composite material including a polymeric matrix and reinforcing fibers; and phosphorescent particles dispersed within the polymer matrix, the phosphorescent particles being configured to emit visible light for about 5 minutes to about 10 minutes following activation by a standard dental curing lamp operating in the 400 nm-500 nm spectrum. In an embodiment, the phosphorescent particles can include europium-doped strontium aluminate. In an embodiment, phosphorescent particles are uniformly dispersed throughout the polymer matrix.

According to an embodiment, a phosphorescent endodontic post includes a fiber-reinforced composite material including a polymeric matrix and reinforcing fibers; and phosphorescent particles dispersed throughout the polymer matrix, the phosphorescent particles being configured to emit visible light for about 5 minutes to about 10 minutes following activation by a standard dental curing lamp operating in the 400 nm-500 nm spectrum. In an embodiment, the phosphorescent particles are dispersed uniformly throughout the post. In an embodiment, a concentration of phosphorescent particles is lower in a coronal portion of the post where mechanical strength is prioritized, and higher in an apical post portion of the post where enhanced visibility is critical during retreatment procedures. In an embodiment, a concentration of phosphorescent particles in the coronal post portion is about 6% to about 10% by weight. In an embodiment, a concentration of phosphorescent particles in the apical post portion is about 10% to about 15% by weight. In an embodiment, the phosphorescent particles can include europium-doped strontium aluminate.

According to an embodiment, a phosphorescent endodontic post includes a fiber-reinforced composite material including a polymeric matrix and reinforcing fibers; and phosphorescent particles confined to a core portion of the post, the phosphorescent particles covering about 15% to about 40% of a cross-sectional area of the post and spaced from an edge portion of the post, thereby maintaining optimized mechanical properties in an area shell region surrounding the core portion of the post.

These and other features of the present subject matter will become readily apparent upon further review of the following specification.

BRIEF DESCRIPTION OF DRAWINGS

Similar reference characters denote corresponding features consistently throughout the attached drawings.

DETAILED DESCRIPTION

Figure 1:
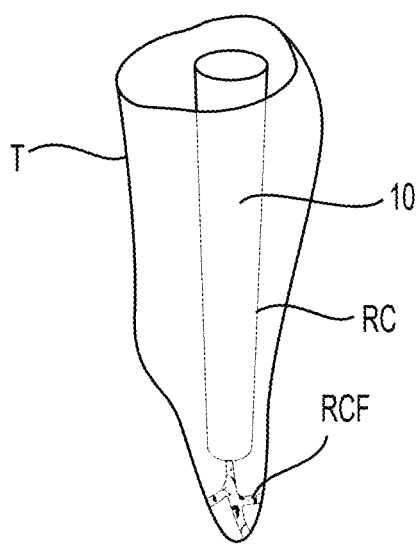
FIG. 1 is a transparent view of a tooth and the phosphorescent endodontic post of the present teachings installed therein.

Throughout the application, where products are described as having, including, or comprising specific components, or where processes or methods are described as having, including, or comprising specific process or method steps, it is contemplated that products of the present teachings can also consist essentially of, or consist of, the recited components, and that the processes or methods of the present teachings can also consist essentially of, or consist of, the recited process or method steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a product or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

The term "optional" or "optionally" means that the subsequently described event or circumstance may or may not occur, and that the description includes instances where said event or circumstance occurs and instances in which it does not.

Unless defined otherwise, all technical and scientific terms used herein have the same meaning as commonly understood to one of ordinary skill in the art to which the presently described subject matter pertains.

Where a range of values is provided, for example, length ranges or width ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

According to an embodiment, a phosphorescent endodontic post 10 includes a fiber-reinforced composite material including a polymeric matrix, reinforcing fibers, and phosphorescent particles dispersed within the polymer matrix. The phosphorescent endodontic post 10 can be installed within a root canal RC of a tooth T having a root canal filling RCF, as shown in FIG. 1. Phosphorescent properties of the phosphorescent endodontic post 10 can facilitate identification of the post 10 during retreatment procedures, which can reduce procedural time and minimize the risk of iatrogenic errors compared to conventional fiber posts, while maintaining all functional benefits of traditional fiber posts. Once installed in a tooth T, the phosphorescent endodontic post 10 can emit visible light for about 5 minutes to about 10 minutes following activation by a standard dental curing lamp operating in the 400 nm-500 nm spectrum. In an embodiment, the phosphorescent particles can include europium-doped strontium aluminate.

Figure 2:
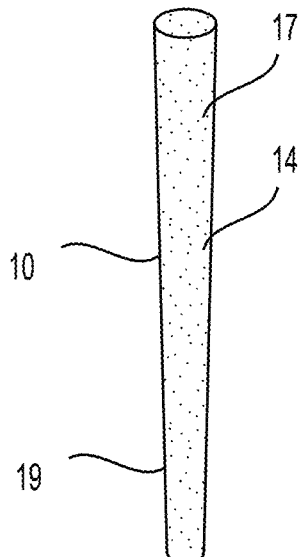
FIG. 2 is a perspective, transparent view of an embodiment of the phosphorescent endodontic post having a uniform distribution of phosphorescent particles throughout the post structure.

In an embodiment, the phosphorescent particles 14 are uniformly dispersed throughout the entire post 10, from a coronal portion 17 to an apical portion 19 of the post and have a concentration ranging from about 6% by weight to about 15% by weight, as shown in FIG. 2. This concentration range can provide optimal balance between visibility enhancement and mechanical integrity. Based on materials science principles, concentrations below about 6% can produce insufficient luminescence for reliable visualization, while concentrations exceeding about 15% can compromise the mechanical properties of the post beyond acceptable clinical thresholds.

Figure 3:
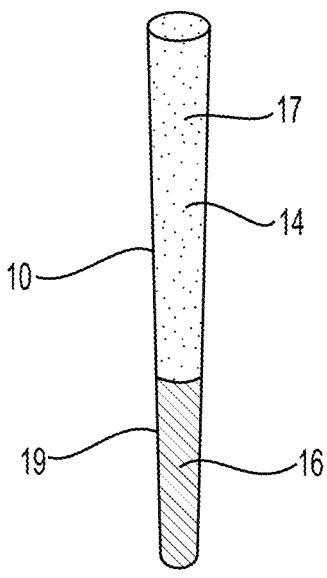
FIG. 3 is a perspective, transparent view of an embodiment of the phosphorescent endodontic post having a gradient distribution of the phosphorescent particles throughout the post structure.
Figure 4:
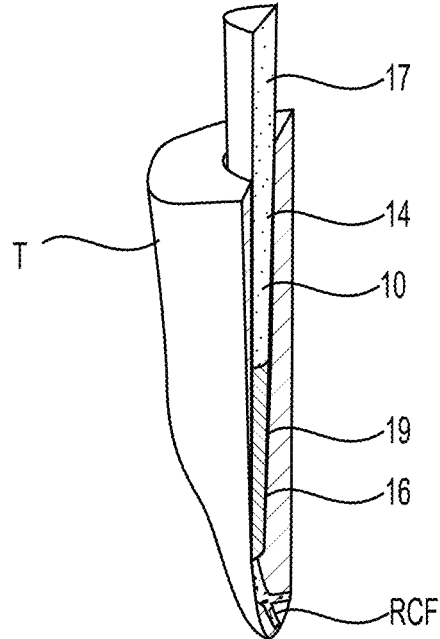
FIG. 4 is a longitudinal, sectional view of the embodiment of the endodontic post of FIG. 3 installed in a tooth.

In an embodiment, the phosphorescent particles are dispersed in a gradient fashion within the polymer matrix, including a lower concentration of phosphorescent particles 14 in a coronal post portion 17 where mechanical strength is prioritized and a higher concentration of phosphorescent particles 16 in an apical post portion 19 where enhanced visibility is critical during retreatment procedures, as shown in FIGS. 3-4.

In an embodiment, a concentration of phosphorescent particles in the coronal post portion 17 is about 6% to about 10% by weight and a concentration of phosphorescent particles in the apical post portion 19 is about 10% by weight to about 15% by weight.

In an embodiment, a concentration of phosphorescent particles in a coronal post portion 17 is about 6% by weight to about 10% by weight, prioritizing mechanical strength in this region that bears the greatest masticatory loads. In an embodiment, a concentration of phosphorescent particles in an apical post portion 19 is about 10% by weight to about 15% by weight, maximizing visibility in the deepest region of the root canal where visibility is most critical during retreatment procedures. In some embodiments, a concentration of phosphorescent particles in a middle post portion (between the coronal post portion and the apical post portion) can be about 8% by weight to about 12% by weight concentration, thereby providing a transitional zone.

This gradient distribution of phosphorescent particles in the polymer matrix can optimize the post 10 for both its primary function of supporting the coronal restoration and its secondary function of facilitating safe removal during retreatment.

Figure 5:
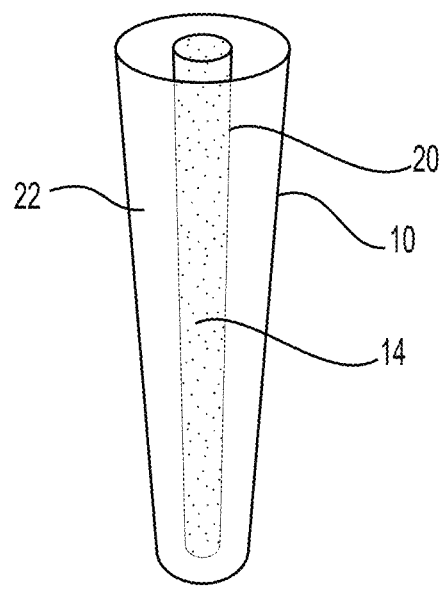
FIG. 5 is a perspective, transparent view of an embodiment of the phosphorescent endodontic post having the phosphorescent particles concentrated within a core of the post structure.

According to an embodiment, the phosphorescent particles can be confined to a core region of the post and be spaced from an edge of the post, providing a core region including phosphorescent particles and a shell region without phosphorescent particles or a reduced concentration of phosphorescent particles, as shown in FIG. 5 and referred to herein as a "core-shell architecture". The core-shell architecture can maintain optimized mechanical properties in the shell region surrounding the core region of the post. When confined to the core region of the post, the phosphorescent particles can cover about 15% to about 40% of a cross-sectional area of the post.

Figure 6:
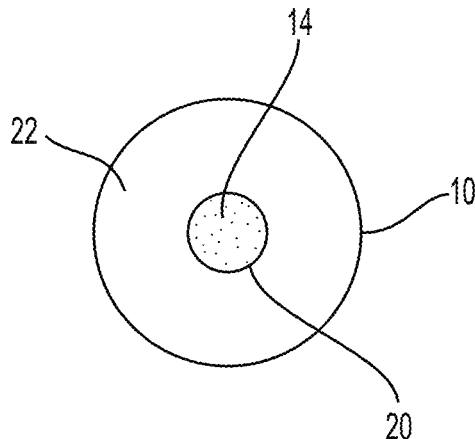
FIG. 6 is a top view of the embodiment of the endodontic post of FIG. 5.

An embodiment of a core-shell architecture can include a longitudinal inner core region including phosphorescent particles at a concentration ranging from about 12% by weight to about 20% by weight; and a shell region surrounding the core region and having a reduced concentration of phosphorescent particles ranging from about 3% by weight to about 8% by weight or no phosphorescent particles, maximizing the mechanical properties of this outer or shell region. The core region can occupy about 15% by weight to about 40% by weight of a total cross-sectional area of the post 10 and run centrally through the entire length of the post, as depicted in the longitudinal view (FIG. 5) and cross-sectional view (FIG. 6).

The core-shell architecture can provide a highly visible "guiding light" effect during retreatment while maintaining optimal mechanical properties in the outer shell that interfaces with dentin and restorative materials.

In an embodiment, the phosphorescent particles can include europium-doped strontium aluminate ($SrAl_2O_4$: $Eu^{2+}$). Europium-doped strontium aluminate ($SrAl_2O_4$: $Eu^{2+}$) can provide: excitation compatibility with standard dental curing lights (400-500 nm); emission wavelength (approximately 520 nm, producing a green glow) that would contrast effectively with tooth structure; extended afterglow duration of 5-10 minutes, providing sufficient working time for clinical procedures; biocompatibility in dental applications; and chemical stability within the polymeric matrix.

According to an embodiment, the polymeric matrix is selected from the group consisting of bisphenol A-glycidyl methacrylate (Bis-GMA) and epoxy resin. In an embodiment, the polymeric matrix can include other dental-grade polymers with demonstrated biocompatibility and clinical longevity.

In an embodiment, the reinforcing fibers can include a material selected from the group consisting of glass, quartz, and polyethylene fibers, providing mechanical strength and an elastic modulus approximating natural dentin.

According to an embodiment, a phosphorescent endodontic post 10 includes a fiber-reinforced composite material defined by a polymeric matrix and reinforcing fibers; and phosphorescent particles uniformly dispersed throughout the polymer matrix. In one embodiment, the phosphorescent particles can be uniformly dispersed throughout the polymer matrix and have a concentration ranging from about 6% by weight to about 15% by weight. In another embodiment, a concentration of phosphorescent particles in a coronal portion of the post can be less than a concentration of phosphorescent particles in an apical portion of the post. For example, the concentration of phosphorescent particles in the coronal portion of the post can range from about 6% to about 10% by weight and a concentration of phosphorescent particles in the apical portion of the post ranges from about 10% to about 15% by weight. The phosphorescent particles can be configured to emit visible light for about 5 minutes to about 10 minutes following activation by a standard dental curing lamp operating in the 400 nm-500 nm spectrum. In an embodiment, the phosphorescent particles can include europium-doped strontium aluminate.

According to an embodiment, a phosphorescent endodontic post includes a fiber-reinforced composite material including a polymeric matrix and reinforcing fibers; and a gradient distribution of phosphorescent particles dispersed within the polymer matrix, with a lower concentration of phosphorescent particles in a coronal post portion where mechanical strength is prioritized, and a higher concentration of phosphorescent particles in an apical post portion where enhanced visibility is critical during retreatment procedures. In an embodiment, a concentration of phosphorescent particles in the coronal post portion is about 6% by weight to about 10% by weight. In an embodiment, a concentration of phosphorescent particles in the apical post portion is about 10% by weight to about 15% by weight. The phosphorescent particles are configured to emit visible light for about 5 minutes to about 10 minutes following activation by a standard dental curing lamp operating in the 400 nm-500 nm spectrum. In an embodiment, the phosphorescent particles can include europium-doped strontium aluminate.

According to an embodiment, a phosphorescent endodontic post includes a fiber-reinforced composite material including a polymeric matrix and reinforcing fibers; and phosphorescent particles confined to a core portion of the post. In an embodiment, the phosphorescent particles cover about 15% to about 40% of a cross-sectional area of the post and are spaced from an edge portion of the post, thereby maintaining optimized mechanical properties in an area shell region surrounding the core portion of the post. The phosphorescent particles are configured to emit visible light for about 5 minutes to about 10 minutes following activation by a standard dental curing lamp operating in the 400 nm-500 nm spectrum. In an embodiment, the phosphorescent particles can include europium-doped strontium aluminate.

Europium-doped strontium aluminate can provide biocompatibility, long afterglow properties, and an emission wavelength of approximately 520 nm that contrasts effectively with dental tissues.

The phosphorescent endodontic post maintains critical mechanical properties of conventional fiber posts, including an elastic modulus of 18-25 GPa (closely matching natural dentin), tensile strength of 1000-1200 MPa, and flexural strength sufficient for clinical function. The phosphorescent properties of the phosphorescent endodontic post can facilitate post identification during retreatment procedures, which can reduce procedural time and minimize the risk of iatrogenic errors compared to conventional fiber posts, while maintaining all functional benefits of traditional fiber posts.

The phosphorescent endodontic post can offer additional advantages through compatibility with contemporary endodontic technologies, including Cone Beam Computed Tomography (CBCT) guidance and laser-assisted removal techniques (such as erbium:YAG laser systems), enhancing the effectiveness of these advanced technologies.

The phosphorescent endodontic post can be manufactured through a process that varies slightly depending on the embodiment. For uniform distribution of the phosphorescent particles, the phosphorescent particles can be treated with a silane coupling agent to enhance chemical bonding with the polymeric matrix and dispersed uniformly throughout the uncured polymeric resin at the specified concentration (6%-

15% by weight) using high-shear mixing under controlled temperature conditions. Then, reinforcing fibers can be incorporated into the phosphorescent-infused resin using established fiber-wetting techniques to ensure complete impregnation and minimize void formation. The composite material can be formed into standardized post shapes by extrusion or molding processes. The formed posts can undergo a controlled curing protocol using light activation (for light-curable resins) or thermal processing (for thermo-setting resins) to achieve optimal polymerization and mechanical properties.

For gradient distribution, three separate batches of resin can be prepared with different concentrations of phosphorescent particles (6-10%, 8-12%, and 10-15% by weight). A specialized co-extrusion process or sequential molding technique can be employed to create a seamless gradient of concentration from the coronal to the apical end of the post. The gradient post can be cured using a protocol that preserves the concentration gradient while ensuring complete polymerization.

For the core-shell design, the core material can be prepared with 12-20% by weight phosphorescent particles and appropriate reinforcing fibers. The shell material can be prepared with a phosphorescent particle concentration ranging from about 3% to about 8% phosphorescent particles or without phosphorescent particles. A co-extrusion process can be used to simultaneously form the core and shell components. The composite structure can be cured to create a fully integrated core-shell post. The resulting posts may be produced in various diameters (typically about 1.0 to about 2.0 mm) and tapers (about 2% to about 10%) to accommodate diverse clinical requirements.

According to an embodiment, the phosphorescent endodontic post can be placed within the prepared root canal using standard clinical protocols, including adhesive cementation. When intact, the post functions identically to conventional fiber posts, providing support for the coronal restoration while exhibiting an elastic modulus compatible with root dentin.

When removal of the endodontic post becomes necessary, the clinician can activate the phosphorescent properties by directing a standard dental curing light (400-500 nm wavelength) toward the exposed portion of the post for 5-10 seconds. This activation can cause the phosphorescent particles to absorb and store energy, which would subsequently be released as visible light (approximately 520 nm) over a period of 5-10 minutes: more precise identification of the post-dentin interface; reduced risk of inadvertent dentin removal; lower likelihood of procedural errors including perforation, gouging, and false canal creation; potentially decreased procedural time; and conservation of root structure critical for long-term prognosis.

Each of the embodiments can offer specific advantages during retreatment. In an embodiment, the post having a uniform particle distribution can provide consistent visibility throughout the entire post structure. In an embodiment, the post having a gradient particle distribution can optimize visibility where it is most needed (apical region) while maintaining maximum strength in the coronal region. In an embodiment, the post with the core-shell design can create a highly visible central marker while preserving optimal mechanical properties in the load-bearing outer shell.

Based on theoretical principles of biomaterials and dental materials science, an embodiment of the phosphorescent endodontic post is expected to exhibit the following performance characteristics: luminescence duration: about 5 minutes to about 10 minutes following activation with a standard dental curing light (about 400 nm to about 500 nm); emission wavelength: approximately 520 nm (green-blue visible spectrum); mechanical properties comparable to conventional fiber posts, including a flexural strength: >900 MPa; an elastic modulus of 18-25 GPa; a tensile strength of 1000-1200 MPa; and fatigue resistance consistent with conventional fiber posts.

The phosphorescent properties of the inventive post can be expected to enhance its compatibility with contemporary endodontic technologies, including:

1. CBCT Navigation Systems: The phosphorescent post would potentially provide a visible reference point that complements the radiographic visibility of CBCT, enabling more accurate correlation between radiographic and clinical visualization during guided post removal;

2. Laser-Assisted Removal: When used in conjunction with erbium:YAG laser systems for post removal, the phosphorescent properties could facilitate more precise laser targeting, potentially reducing the risk of unintended laser effects on surrounding dentin; and 3. Magnification Systems: Under microscopic or loupe magnification, the phosphorescent glow is expected to create enhanced contrast that would improve the effectiveness of optical magnification.

It is to be understood that the phosphorescent endodontic post is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

What is claimed:

1. A phosphorescent endodontic post, said phosphorescent endodontic post having an elongated post shape, said elongated post shape having a coronal post portion and an apical post portion, said post shape of the phosphorescent endodontic post comprising:

a fiber-reinforced composite material including a polymeric matrix and reinforcing fibers; and phosphorescent particles dispersed within the polymeric matrix, the phosphorescent particles being configured to emit visible light for about 5 minutes to about 10 minutes following activation by a standard dental curing lamp operating in the 400 nm-500 nm spectrum, wherein the phosphorescent particles have a concentration range of about 6% to about 15% by weight.

2. The phosphorescent endodontic post of claim 1, wherein the phosphorescent particles comprise europium-doped strontium aluminate.

3. The phosphorescent endodontic post of claim 1, wherein the polymeric matrix comprises a material selected from the group consisting of bisphenol A-glycidyl methacrylate (Bis-GMA) and epoxy resin.

4. The phosphorescent endodontic post of claim 1, wherein the reinforcing fibers comprise a material selected from the group consisting of glass, quartz, and polyethylene fibers.

5. The phosphorescent endodontic post of claim 1, wherein the phosphorescent particles are uniformly dispersed throughout the polymer matrix.

6. The phosphorescent endodontic post of claim 1, wherein the concentration of phosphorescent particles in the coronal portion of the post is less than the concentration of phosphorescent particles in the apical portion of the post.

7. The phosphorescent endodontic post of claim 6, wherein the concentration of phosphorescent particles in the coronal portion of the post ranges from about 6% to about 10% by weight.

8. The phosphorescent endodontic post of claim 7, wherein the concentration of phosphorescent particles in the apical portion of the post ranges from about 10% to about 15% by weight.

9. The phosphorescent endodontic post of claim 1, wherein the phosphorescent particles are confined to a core portion of the post and spaced from an edge portion of the post.

10. The phosphorescent endodontic post of claim 1, wherein the phosphorescent particles cover about 15% to about 40% of a cross-sectional area of the post.

11. A phosphorescent endodontic post, said phosphorescent endodontic post having an elongated post shape, said elongated post shape having a coronal post portion and an apical post portion, said post shape of the phosphorescent endodontic post comprising:

a fiber-reinforced composite material including a polymeric matrix and reinforcing fibers; and phosphorescent particles dispersed throughout the polymer matrix, the phosphorescent particles being configured to emit visible light for about 5 minutes to about 10 minutes following activation by a standard dental curing lamp operating in the 400 nm-500 nm spectrum.

12. The phosphorescent endodontic post of claim 11, wherein the phosphorescent particles comprise europium-doped strontium aluminate.

13. The phosphorescent endodontic post of claim 11, wherein the phosphorescent particles have a concentration ranging from about 6% to about 15% by weight.

14. The phosphorescent endodontic post of claim 11, wherein a concentration of phosphorescent particles in a coronal portion of the post is less than a concentration of phosphorescent particles in an apical portion of the post.

15. The phosphorescent endodontic post of claim 14, wherein the concentration of phosphorescent particles in the coronal portion of the post ranges from about 6% to about 10% by weight.

16. The phosphorescent endodontic post of claim 14, wherein a concentration of phosphorescent particles in the apical portion of the post ranges from about 10% to about 15% by weight.

17. The phosphorescent endodontic post of claim 14, wherein the phosphorescent particles comprise europium-doped strontium aluminate.

18. A phosphorescent endodontic post, said phosphorescent endodontic post having an elongated post shape, said elongated post shape having a coronal post portion and an apical post portion, said post shape of the phosphorescent endodontic post comprising:

a fiber-reinforced composite material including a polymeric matrix and reinforcing fibers; and phosphorescent particles confined to a core portion of the post.

19. The phosphorescent endodontic post of claim 18, wherein the phosphorescent particles cover about 15% to about 40% of a cross-sectional area of the post.

20. The phosphorescent endodontic post of claim 18, wherein the phosphorescent particles comprise europium-doped strontium aluminate.

* * * * *